United States Patent
Rubin

(10) Patent No.: US 6,372,197 B1
(45) Date of Patent: *Apr. 16, 2002

(54) METHODS AND COMPOSITIONS USING NORASTEMIZOLE IN COMBINATION WITH LEUKOTRIENE INHIBITORS

(75) Inventor: Paul D. Rubin, Sudbury, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/721,668

(22) Filed: Nov. 27, 2000

Related U.S. Application Data

(63) Continuation of application No. 09/059,572, filed on Apr. 14, 1998, now Pat. No. 6,248,308.

(51) Int. Cl.$^7$ .............................. A61K 9/12
(52) U.S. Cl. .................... 424/45; 424/46; 424/464; 424/443; 514/290; 514/322; 514/212
(58) Field of Search .................. 424/46, 45, 78.02, 424/464, 443; 514/290, 322, 212

(56) References Cited

U.S. PATENT DOCUMENTS

| | | | |
|---|---|---|---|
| 5,714,501 A | | 2/1998 | Timmerman et al. ....... 514/325 |
| 5,869,479 A | * | 2/1999 | Kreutner et al. ............ 514/212 |
| 5,900,421 A | | 5/1999 | Handley et al. ............ 514/290 |
| 6,130,233 A | * | 10/2000 | Woosley et al. ............ 514/322 |

FOREIGN PATENT DOCUMENTS

| | | |
|---|---|---|
| EP | 0780127 | 6/1997 |
| WO | WO 97/28797 | 8/1997 |
| WO | WO 97/46243 | 12/1997 |
| WO | WO 99/32125 | 7/1999 |

OTHER PUBLICATIONS

F–D–C Reports, 1998, "Trade and Govt. Memos", Feb. 9, 1998.

Physician's Desk Reference, 1998, pp. 303, 474–476, 3148–3149.

Roquet, A. et al., 1997, "Combined Antagonism of Leukotrienes and Histamine Produces Predominant Inhibition of Allergen–Induced Early and Late Phase Airway Obstruction in Asthmatics", Am. J. Respir. Crit. Care Med., 155:1856–1863.

Zhang, M.Q. & Timmerman, H., 1997, "Leukotriene cysLT1 (LTD4) receptor antagonism of H1–antihistamines: An in vitro study", Inflamm. Res., 46(1):S93–S94.

Baroody, F.M., 1996, "Effects of Loratadine and Terfenadine on the Induced Nasal Allergic Reaction", Arch. Otolaryngol. Head and Neck Surg., 122:309–316.

Ku, Y. et al., 1996, "Effects of Histamine H1 Receptor Antagonists on Action Potentials in Guinea–Pig Isolated Papillary Muscles", Arch. Int. Pharmacodyn., 331:59–73.

Merk Index, Twelfth Edition, 1996, 6340, Montelukast, p. 1070.

Miadonna et al., 1994, "Inhibitory Effect of the $H_1$ Antagonist Loratadine on Histamine Release from Human Basophils", Int. Arch. Allergy Immunol. 105:12–17.

Temple et al., 1988, "Loratadine, an Antihistamine, Blocks antigen– and lonophore—Induced Leukotriene Release From Human Lung In Vitro", Prostaglandins 35(4):549–554.

* cited by examiner

Primary Examiner—Diana Dudash
Assistant Examiner—M. Haghighatian

(57) ABSTRACT

Methods and pharmaceutical compositions employing norastemizole and a leukotriene inhibitor for the treatment or prevention of inflammation or allergic disorders, such as asthma or the symptoms thereof. Also included are methods and compositions employing norastemizole and a decongestant for the treatment or prevention of inflammation or allergic disorders, such as asthma or the symptoms thereof.

12 Claims, No Drawings

METHODS AND COMPOSITIONS USING NORASTEMIZOLE IN COMBINATION WITH LEUKOTRIENE INHIBITORS

This application is a continuation of Ser. No. 09/059,572, filed Apr. 14, 1998, now U.S. Pat. No. 6,248,308.

1. FIELD OF THE INVENTION

The invention relates to methods of treating asthma, inflammation, and allergic conditions. In another aspect, this invention relates to the use of antihistamines and leukotriene inhibitors, and compositions containing them.

2. BACKGROUND OF THE INVENTION

Astemizole is an antagonist of the H-1 histamine receptor protein, which mediates the response antagonized by conventional antihistamines. Astemizole is well absorbed but is extensively metabolized. See Uchiyama et al., *Pharmarcometrics*, 40:7793 (1990). Three main metabolites have been identified, all of which are reported to have some antihistaminic activity. See Kamei et al., *Arzneimittel-Forschung/Drug Research*, 41:932–36 (1991).

Weintraub et al., *Hosp. Formul.*, 22:918–27 (1987) describes clinical efficacy of astemizole in the treatment of both seasonal and perennial allergies. It has also been suggested that astemizole would be useful for the treatment of asthma.

Astemizole is sold commercially as a prescription antihistamine (HISMANAL®), however, the use of astemizole is believed to have a potential for serious cardiotoxicity in certain patients. Norastemizole, one of the metabolites of astemizole, is said to have the beneficial effects of astemizole while having a reduced risk of cardiotoxicity. The preparation of norastemizole is described, e.g.; in WO 94/07495, published Apr. 14, 1994.

Leukotrienes augment neutrophil and eosinopil migration, neutrophil and monocyte aggregation, leukocyte adhesion, increase capillary permeability, and smooth muscle 35 contraction, all of which contribute to inflammation, edema, mucus secretion, and bronchoconstriction. For example, zileuton, sold commercially as ZYFLO®, is a specific inhibitor of 5-lipoxygenase having the chemical name (±)-1-(1-Benso[b]thien-2-ylethyl)-1-hydroxyurea. Zileuton is known to inhibit leukotriene ($LTH_4$, $LTC_4$, $LTD_4$, and $LTE_4$) formation in vitro. Zileuton is an inhibitor ex vivo of $LTB_4$ formation in several species and inhibits leukotriene-dependent smooth muscle contractions in vitro in guinea pig and human airways. One study of 373 patients indicated that 600 mg of zileuton four times daily were required to provide efficacy, while 400 mg failed to do so. In some patients, zileuton was reported to cause headache, pain, asthenia, dyspepsia, nausea, and myalgia. [Physician's Desk Reference, 52 ed., Medical Economics Co., Inc., 474–76 (1998)].

Zafirlukast, sold commercially as ACCOLATE®, is another type of leukotriene inhibitor. This leukotriene inhibitor is a leukotriene receptor antagonist (LTRA) of leukotriene $D_4$ and $E_4$, and has the chemical name 4-(5-cyclopentyloxy-carbonylamino-1-methyl-indol-8-ylmethyl)-3-methoxy-N-o-tolylsulfonylbenzamide. Cysteinyl leukotriene production and receptor occupation have been correlated with the pathophysiology of asthma. In vitro studies indicated that zafirlukast antagonized the contractile activity of three leukotrienes in conducting airway smooth muscle from laboratory animals and humans; prevented intradermal $LTD_4$-induced increases in cutaneous vascular permeability; and inhibited inhaled $LTD_4$-induced influx of eosinophils into animal lungs. In some patients, zafirlukast has been reported to cause headache, infection, nausea, diarrhea, pain, asthenia, abdominal pain, dizziness, myalgia, fever, vomiting, SGPT elevation, and dyspepsia. [Physician's Desk Reference, 52 ed., Medical Economics Co., Inc., 3148–49 (1998)].

3. SUMMARY OF THE INVENTION

The present invention represents an improvement over the astemizole and norastemizole, as well as the leukotriene inhibitor, technology presently available.

This invention relates to novel pharmaceutical compositions containing (a) norastemizole, or a pharmaceutically acceptable salt thereof, and (b) a leukotriene inhibitor, or a pharmaceutically acceptable salt thereof, and optionally (c) a decongestant, and a pharmaceutically acceptable carrier or excipient.

The compositions of the invention employing norastemizole and a leukotriene inhibitor, and optionally a decongestant, possess potent antihistaminic activity and are useful in treating, preventing, or managing asthma, asthma symptoms, inflammation, allergic rhinitis, and other allergic disorders, as well as dermatitis. The compositions employing norastemizole and a leukotriene inhibitor provide an improved overall therapy relative to either norastemizole or the leukotriene inhibitor alone. Additionally, the novel pharmaceutical compositions of the invention are useful in treating, preventing, or managing motion sickness, vertigo, diabetic retinopathy, small vessel complications due to diabetes and such other conditions as may be related to the activity of the norastemizole as an antagonist of the H-1 histamine receptor. The compositions of the invention are also useful in combination with non-steroidal anti-inflammatory agents or other non-narcotic analgesics, and are useful for the treatment of cough, cold, cold-like, and/or flu symptoms and the discomfort, headache, pain, fever, and general malaise associated therewith. The aforementioned combinations (e.g., norastemizole and a leukotriene inhibitor) may optionally include one or more other active components including a decongestant, cough suppressant/antitussive, or expectorant.

The compositions of the invention can be used to treat, prevent, or manage the disorders described herein while reducing or avoiding adverse effects associated with administration of other non-sedating antihistamines, such as astemizole.

In one embodiment, this invention provides a method of preventing or treating asthma or the symptoms of asthma in a human which comprises administering to a human a therapeutically effective amount of norastemizole, or a pharmaceutically acceptable salt thereof, and a therapeutically effective amount of a leukotriene inhibitor, or a pharmaceutically acceptable salt thereof.

The invention also provides a method of treating or preventing asthma or the symptoms of asthma in a human which comprises administering to a human a composition, said composition comprising (i) a therapeutically effective amount of norastemizole or a pharmaceutically acceptable salt thereof; (ii) a leukotriene inhibitor selected from the group consisting of 5-lipoxygenase inhibitors, 5-lipoxygenase activating protein antagonists, and leukotriene receptor antagonists, or a pharmaceutically acceptable salt thereof; (iii) optionally a therapeutically effective amount of a decongestant; and a pharmaceutically acceptable carrier or excipient.

This invention also includes a method of preventing or treating asthma or the symptoms of asthma in a human which comprises administering to a human a therapeutically effective amount of norastemizole, or a pharmaceutically acceptable salt thereof, a therapeutically effective amount of a leukotriene inhibitor, or a pharmaceutically acceptable salt thereof, and a therapeutically effective amount of a decongestant.

In a second embodiment, the invention also provides for a method of preventing or treating allergic rhinitis in a human which comprises administering to a human a therapeutically effective amount of norastemizole, or a pharmaceutically acceptable salt thereof, and either a leukotriene inhibitor or a decongestant, or both, such that all three active ingredients are used.

In a third embodiment, the invention also provides for a method of preventing or treating dermatitis in a human which comprises administering to a human a therapeutically effective amount of norastemizole, or a pharmaceutically acceptable salt thereof, and either a leukotriene inhibitor or a decongestant, or both, such that all three active ingredients are used.

In a fourth embodiment, the invention also provides for a method of preventing or treating inflammation in a human which comprises administering to a human a therapeutically effective amount of norastemizole, or a pharmaceutically acceptable salt thereof, and a leukotriene inhibitor, or a pharmaceutically acceptable salt thereof.

The invention also provides a method of preventing or treating inflammation in a human which comprises administering to a human a composition, said composition comprising (i) a therapeutically effective amount of norastemizole or a pharmaceutically acceptable salt thereof; (ii) a leukotriene inhibitor selected from the group consisting of 5-lipoxygenase inhibitors, 5-lipoxygenase activating protein antagonists, and leukotriene receptor antagonists, or a pharmaceutically acceptable salt thereof; (iii) optionally a therapeutically effective amount of a decongestant; and a pharmaceutically acceptable carrier or excipient.

This invention also includes a method of preventing or treating inflammation in a human which comprises administering to a human a therapeutically effective amount of norastemizole, or a pharmaceutically acceptable salt thereof, a therapeutically effective amount of a leukotriene inhibitor, or a pharmaceutically acceptable salt thereof, and a therapeutically effective amount of a decongestant.

In a fifth embodiment, the invention also provides for a method of preventing or treating a condition responsive to leukotriene inhibition in a human which comprises administering to a human a therapeutically effective amount of norastemizole, or a pharmaceutically acceptable salt thereof, and either a leukotriene inhibitor or a decongestant, or both, such that all three active ingredients are used.

The invention encompasses the treatment, prevention and/or management of asthma or the symptoms of asthma, allergic rhinitis, inflammation, or dermatitis using a metabolite of astemizole, preferably norastemizole, and a leukotriene inhibitor. The invention also encompasses the treatment, prevention, and/or management of these disorders with norastemizole and a decongestant. Further, the invention encompasses the treatment, prevention and/or management of these disorders using norastemizole, a leukotriene inhibitor, and a decongestant. The invention encompasses the treatment, prevention, and/or management of these disorders using a single unit dosage form (solid or liquid; preferably a solid) that contains norastemizole and either a leukotriene inhibitor or a decongestant, or all three active ingredients. However, it should be recognized that combination therapy by separate administration of each active ingredient is also contemplated. The methods and compositions of this invention are believed to reduce or avoid adverse effects associated with administration of non-sedating antihistamines, such as astemizole. The methods and compositions described herein are believed to provide superior or improved therapy over prior art methods and compositions involving norastemizole in the absence of a leukotriene inhibitor, or a leukotriene inhibitor in the absence of norastemizole. Without being limited by theory, it is believed that the combination of norastemizole, a leukotriene inhibitor, and optionally a decongestant, provides superior, improved, and synergistic effects unachievable by any of these compounds alone.

4. DETAILED DESCRIPTION OF THE INVENTION

The administration of norastemizole, a leukotriene inhibitor, and optionally a decongestant, in the methods of the present invention may be made either concurrently or sequentially, i.e., norastemizole, a leukotriene inhibitor, and an optional decongestant may be administered as a combination, concurrently but separately, or by the sequential administration, e.g., of norastemizole, leukotriene inhibitor, and decongestant, or the sequential administration of a leukotriene inhibitor, decongestant, and norastemizole. The compositions administered in each of these methods may be concurrent, sequential, or in any combination of concurrent and/or sequential.

The major adverse effects to be avoided by the methods and compositions of the present invention include, but are not limited to, cardiotoxicity, such as cardiac arrythmia.

Astemizole and other non-sedating antihistamines have antihistaminic activity and provide therapy and a reduction of symptoms for a variety of conditions and disorders related to allergic rhinitis and other allergic disorders, diabetes mellitus, and other conditions; however, such drugs, while offering the expectation of efficacy, may cause adverse effects. Utilizing norastemizole in combination with a leukotriene inhibitor, and optionally with a decongestant, results in clearer dose-related definitions of efficacy, diminished adverse effects, a superior therapy due to synergistic activity, and accordingly, an improved therapeutic index. It is, therefore, more desirable to use the compositions and methods of the invention than to use astemizole, or norastemizole, itself or other non-sedating antihistamines. Norastemizole and its salts can be synthesized, for example, as described in U.S. Pat. Nos. 4,835,161, 4,556,660, and 4,219,559, which are expressly incorporated herein by reference thereto for this purpose.

The term "adverse effects" as used herein includes, but is not limited to, cardiac arrhythmias, cardiac conduction disturbances, appetite stimulation, weight gain, sedation, gastrointestinal distress, headache, dry mouth, constipation, and diarrhea. The term "cardiac arrhythmias" includes, but is not limited to, ventricular tachyarrhythmias, torsades de pointes, and ventricular fibrillation.

The phrase "therapeutically effective amount of norastemizole" as used herein means that amount of norastemizole which provides a therapeutic benefit in the treatment, management, or prevention of conditions that are responsive to histamine antagonists, such as urticaria, allergic rhinitis, inflammation, symptomatic dermographism, dermatitis, asthma, allergic asthma, retinopathy or other small vessel disorders associated with diabetes mellitus, and the symptoms associated with asthma or allergic rhinitis such as cough, cold, cold-like, wheezing, dyspnea, and/or flu symptoms including, but not limited to, sneezing, rhinorrhea, lacrimation, and dermal irritation.

The phrase "therapeutically effective amount" with respect to leukotriene inhibitor as used herein means that amount of leukotriene inhibitor that provides a therapeutic benefit in the treatment, prevention, or management of conditions that are responsive to leukotriene inhibitors, such as urticaria, allergic rhinitis, inflammation, symptomatic dermographism, dermatitis, asthma, allergic asthma, retinopathy or other small vessel disorders associated with diabetes mellitus, and the symptoms associated with asthma or allergic rhinitis such as cough, cold, cold-like, wheezing, dyspnea, and/or flu symptoms including, but not limited to, sneezing, rhinorrhea, lacrimation, and dermal irritation.

The phrase "therapeutically effective amount" with respect to decongestant as used herein means that amount of decongestant alone, or in combination with other drugs, that provides a therapeutic benefit in the treatment, prevention, or management of any condition that is responsive to decongestants, such as congestion of the respiratory tract and/or the sinuses, and the symptoms associated with congestion, such as cough, cold, cold-like, wheezing, dyspnea, and/or flu symptoms including, but not limited to, sneezing, rhinorrhea, lacrimation, and dermal irritation.

The term "asthma" as used herein is defined as a disorder characterized by increased responsiveness of the trachea and bronchi to various stimuli, which results in symptoms that include, but are not limited to, wheezing, cough, shortness of breath, dyspnea, and the like. Asthma includes, for example, allergic asthma.

The term "dermatitis" as used herein is that disorder caused by inflammation to the skin including endogenous and contact dermatitis such as, but not limited to: actinic dermatitis (or photodermatitis), atopic dermatitis, chemical dermatitis, cosmetic dermatitis, dermatitis aestivalis, and seborrheic dermatitis.

The term "inflammation" as used herein is a fundamental pathologic process of a dynamic complex of cytologic and chemical reactions that occur in the affected blood vessels and adjacent tissues in response to an injury or abnormal stimulation caused by a physical, chemical, or biologic agent, including: the local reactions and resulting morphologic changes; the destruction or removal of the injurious material; and the responses that lead to repair and healing. The typical signs of inflammation are redness, heat or warmth, swelling, pain, and occasionally inhibited or lost function. All of the signs may be observed in certain instances, although any particular sign is not necessarily always present.

The term "leukotriene inhibitor" as used herein includes any agent or compound that inhibits, restrains, retards or otherwise interacts with the action or activity of leukotrienes, such as, but not limited to, 5-lipoxygenase ("5-LO") inhibitors, 5-lipoxygenase activating protein ("FLAP") antagonists, and leukotriene receptor antagonists ("LTRAs"). An exemplary LTRA is leukotriene $D_4$ ("$LTD_4$") receptor antagonist.

The term "5-lipoxygenase inhibitor" or "5-LO inhibitor" as used herein includes any agent or compound that inhibits, restrains, retards or otherwise interacts with the enzymatic action of 5-lipoxygenase, such as, but not limited to, zileuton, docebenone, piripost, and ICI-D2318.

The term "5-lipoxygenase activating protein antagonist" or "FLAP antagonist" as used herein includes any agent or compound that inhibits, restrains, retards or otherwise interacts with the action or activity of 5-lipoxygenase activating protein, such as, but not limited to, MK-591 and MK-886.

The term "leukotriene receptor antagonist" or "LTRA" as used herein includes any agent or compound that inhibits, restrains, retards or otherwise antagonizes the activity of receptors that are responsive to leukotrienes, including those responsive to leukotriene $D_4$. Exemplary LTRAs include, but are not limited to, sodium 1-(((R)-(3-(2-(6,7-difluoro-2-quinolinyl)ethynyl)phenyl)-3-(2-(2-hydroxy-2-propyl) phenyl)thio)methyl)cyclopropaneacetate; 1-(((1(R)-(3-(2-(2,3-dichlorothieno[3,2-b]pyridin-5-yl)-(E)-ethenyl) phenyl)-3-(2-(1-hydroxy-1-methylethyl)phenyl)propyl) thio)methyl)cyclopropaneacetic acid or sodium or other salts thereof, pranlukast, zafirlukast (ICI-204219), and montelukast (MK-476), the latter of which is sold commercially as SINGULAIR®.

The magnitude of a prophylactic or therapeutic dose of norastemizole or leukotriene inhibitor in the acute or chronic management of a disorder or condition will vary with the severity of the condition to be treated and the route of administration. The dose, and perhaps the dose frequency, will also vary according to the age, body weight, and response of the individual patient. Suitable total daily dose ranges can be readily determined by those skilled in the art. In general, the total daily dose range for norastemizole, for the conditions described herein, is from about 1 mg to about 200 mg administered in single or divided doses orally, topically, transdermally, or locally by inhalation. For example, a preferred oral daily dose range should be from about 10 mg to about 100 mg. A preferred oral daily dose range of decongestant, such as pseudoephedrine, should be from about 50 mg to about 300 mg, more preferably, about 150 mg to about 250 mg. In addition, suitable oral daily dosage ranges of leukotriene inhibitor can be readily determined by those skilled in the art. For example, see the Physician's Desk Reference® 1998 for suitable dosages presently used for known leukotriene inhibitors. For example, for 5-lipoxygenase inhibitors, the oral daily dose range should be from about 20 mg to 2,500 mg, preferably from about 20 mg to 800 mg. For leukotriene receptor antagonists, the oral daily dose range should be from about 2 mg to 100 mg, preferably from about 5 mg to 20 mg.

It is further recommended that children, patients aged over 65 years, and those with impaired renal or hepatic function initially receive low doses, and that they then be titrated based on individual response(s) or blood level(s). It may be necessary to use dosages outside these ranges in some cases as will be apparent to those skilled in the art. Further, it is noted that the clinician or treating physician will know how and when to adjust, interrupt, or terminate therapy in conjunction with individual patient response.

The term "therapeutically effective amount of norastemizole or a pharmaceutically acceptable salt thereof" is encompassed by the above-described dosage amounts. In addition, the terms "said composition comprising (i) a therapeutically effective amount of norastemizole or a pharmaceutically acceptable salt thereof; and (ii) "a therapeutically effective amount of a decongestant"; "said composition comprising (i) a therapeutically effective amount of norastemizole or a pharmaceutically acceptable salt thereof; and (ii) a therapeutically effective amount of a leukotriene inhibitor"; and "said composition comprising (i) a therapeutically effective amount of norastemizole or a pharmaceutically acceptable salt thereof; (ii) a therapeutically effective amount of a leukotriene inhibitor; and (iii) a therapeutically effective amount of decongestant" are also encompassed by the above-described dosage amounts and dose frequency schedule.

Any suitable route of administration may be employed for providing the patient with an effective dosage of norastemizole according to the methods of the present invention. For example, oral, intraoral, rectal, parenteral, epicutaneous, transdermal, subcutaneous, intramuscular, intranasal, sublingual, buccal, intradural, intraocular, intrarespiratory, or nasal inhalation and like forms of administration may be employed. Oral administration is generally preferred. For the methods to treat dermatitis, however, topical administration is preferred.

The pharmaceutical compositions used in the methods of the present invention, which are sterile and stable, include norastemizole, the metabolic derivative of astemizole, and either a leukotriene inhibitor, or a decongestant, or both, as the active ingredients, or pharmaceutically acceptable salts thereof. The compositions may also contain a pharmaceutically acceptable carrier or excipient, and optionally, other therapeutic ingredients. The compositions are preferably single solid unit doses, e.g., capsules, tablets, or the like.

The term "pharmaceutically acceptable salt" refers to a salt prepared from pharmaceutically acceptable non-toxic acids or bases including inorganic acids or bases or organic acids or bases. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases include metallic salts made from aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylglucamine), lysine and procaine.

The compositions for use in the methods of the present invention can include suitable excipients or carriers such as starches, sugars, microcrystalline cellulose, diluents, granulating agents, lubricants, binders, disintegrating agents, and the like.

Dosage forms include tablets, troches, dispersions, suspensions, solutions, capsules, patches, gel caps, syrups, elixirs, gels, powders, magmas, lozenges, ointments, creams, pastes, plasters, lotions, discs, suppositories, nasal or oral sprays, aerosols, and the like.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compound for use in the methods of the present invention may also be administered by controlled release means and/or delivery devices such as those described in U.S. Pat. Nos. 3,845,770; 3,916,899; 3,536,809; 3,598,123; and 4,008,719, the disclosures of which are incorporated herein by reference thereto.

Preferred compositions containing norastemizole are lactose free solid oral compositions. Additional preferred suitable compositions containing norastemizole for use according to the invention include non-hygroscopic and anhydrous norastemizole solid oral compositions.

Pharmaceutical compositions for use in the methods of the present invention may be prepared by any of the methods of pharmacy, but all methods include the step of bringing into association the active ingredient(s) with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Preferably, the tablet, cachet or capsule contains either of the following dosages: 15 mg, 30 mg, or 45 mg of norastemizole, in combination with the leukotriene inhibitor and/or decongestant.

The invention is further defined by reference to the following example describing in detail the preparation of the composition and the compositions used in the methods of the present invention, as well as their utility. It will be apparent to those skilled in the art that many modifications, both to materials and methods, may be practiced which are within the scope of this invention.

5. EXAMPLES

5.1 Example 1

Preparation of Norastemizole

Norastemizole may be synthesized, for example, by the methods disclosed in U.S. Pat. Nos. 4,219,559 and 4,835,161, which are hereby incorporated herein by express reference thereto. Norastemizole may also be prepared by the reaction steps disclosed in WO 94/07495, published Apr. 14, 1994. Reaction of an isothiocyanate with phenylenediamine gives a corresponding thiourea. N-Alkylation with p-fluorobenzylbromide gives a secondary amine which, upon cyclization, yields a substituted benzimidazole. Treatment of the benzimidazole with base hydrolyzes the urethane moiety to give norastemizole. N-Alkylation of norastemizole with p-methoxyphenethyl bromide yields astemizole. Astemizole can be converted to desmethylastemizole by demethylation using, for example, a Lewis acid, such as boron trifluoride, boron trichloride, aluminum trichloride, and the like.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited patents or publications may provide further useful information these cited materials are incorporated herein in their entireties by reference thereto.

What is claimed is:

1. A method of treating or preventing asthma or the symptoms thereof in a human which comprises administering to a human a therapeutically effective amount of norastemizole, or a pharmaceutically acceptable salt thereof, and a therapeutically effective amount of a leukotriene inhibitor, or a pharmaceutically acceptable salt thereof.

2. A method of treating or preventing asthma or the symptoms thereof in a human which comprises administering to a human a composition, said composition comprising (i) a therapeutically effective amount of norastemizole, or a pharmaceutically acceptable salt thereof; (ii) a therapeutically effective amount of leukotriene inhibitor, or a pharmaceutically acceptable salt thereof, selected from the group consisting of 5-lipoxygenase inhibitors, 5-lipoxygenase activating protein antagonists, leukotriene receptor antagonists, and mixtures thereof; and a pharmaceutically acceptable carrier or excipient.

3. The method of claim 1, wherein the administration of the amount norastemizole, or a pharmaceutically acceptable salt thereof, and the amount of leukotriene inhibitor, or a pharmaceutically acceptable salt thereof, avoids the concomitant liability of adverse effects associated with the administration of non-sedating antihistamines.

4. The method of claim 2, wherein the administration of the amount norastemizole, or a pharmaceutically acceptable salt thereof, and the amount of leukotriene inhibitor, or a pharmaceutically acceptable salt thereof, avoids the concomitant liability of adverse effects associated with the administration of non-sedating antihistamines.

5. The method of claim 1, 2, 3, or 4 wherein the administering further comprises a therapeutically effective amount of a decongestant, or a pharmaceutically acceptable salt thereof.

6. The method of claim 1 wherein said human has asthma.

7. The method of claim 1, wherein the leukotriene inhibitor is selected from the group consisting of leukotriene $D_4$, zileuton, docebenone, piripost, ICI-D2318, MK-591, MK-886, sodium 1-(((R)-(3-(2-(6,7-difluoro-2-quinolinyl)ethynyl)phenyl)-3-(2-(2-hydroxy-2-propyl)phenyl)thio)methyl)cyclopropane-acetate; 1-(((1(R)-(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid, pranlukast, zafirlukast, and montelukast.

8. The method of claim 1, wherein the therapeutically effective amount of norastemizole or pharmaceutically acceptable salt thereof is administered orally, topically, transdermally, or by inhalation.

9. The method of claim 1, wherein the therapeutically effective amount of the leukotriene inhibitor or pharmaceutically acceptable salt thereof is administered orally, topically, transdermally, or by inhalation.

10. The method of claim 2, wherein the leukotriene inhibitor is selected from the group consisting of leukotriene $D_4$, zileuton, docebenone, piripost, ICI-D2318, MK-591, MK-886, sodium 1-(((R)-(3-(2-(6,7-difluoro-2-quinolinyl)ethynyl)phenyl)-3-(2-(2-hydroxy-2-propyl)phenyl)thio)methyl)-cyclopropane-acetate; 1-(((1(R)-(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropane-acetic acid, pranlukast, zafirlukast, and montelukast.

11. The method of claim 2, wherein the therapeutically effective amount of norastemizole, or pharmaceutically acceptable salt thereof, is administered orally, topically, transdermally, or by inhalation.

12. The method of claim 2, wherein the therapeutically effective amount of the leukotriene inhibitor, or pharmaceutically acceptable salt thereof, is administered orally, topically, transdermally, or by inhalation.

* * * * *